United States Patent [19]

Palson

[11] 4,383,951
[45] May 17, 1983

[54] FORCED FLOW VAPOR DISTRIBUTION DEVICE

[75] Inventor: Richard C. J. Palson, Medfield, Mass.

[73] Assignee: Woodlets, Inc., Buffalo, N.Y.

[21] Appl. No.: 295,846

[22] Filed: Aug. 24, 1981

[51] Int. Cl.³ ............................................... A61L 9/04
[52] U.S. Cl. ...................... 261/30; 261/104; 261/DIG. 65; 239/35; 239/46; 239/56; 239/71; 422/124
[58] Field of Search ............... 261/DIG. 17, DIG. 65, 261/101, 104, 30; 422/123, 124; 239/35, 38, 46, 55, 56, 71; 416/184; 340/636, 376

[56] References Cited

U.S. PATENT DOCUMENTS

| | | | |
|---|---|---|---|
| 1,136,827 | 4/1915 | Montgomery | 416/189 |
| 1,254,337 | 1/1918 | Marsh | 422/124 |
| 2,069,179 | 1/1937 | Dunaway | 299/24 |
| 2,262,772 | 11/1941 | Carsen | 422/124 |
| 2,614,820 | 10/1952 | Boydjieff | 261/26 |
| 2,629,149 | 2/1953 | Yaffe | 422/124 |
| 2,867,866 | 1/1959 | Steele | 422/124 |
| 3,030,615 | 4/1962 | Dinlocker | 340/636 |
| 3,261,544 | 7/1966 | Guichard | 416/189 |
| 3,633,881 | 1/1972 | Yurdin | 261/24 |
| 3,804,592 | 4/1974 | Garbe | 21/121 |
| 3,894,665 | 7/1975 | Swenson | 222/402.11 |
| 3,967,762 | 7/1976 | Machon | 222/321 |
| 3,990,848 | 11/1976 | Corris | 21/126 |
| 3,993,444 | 11/1976 | Brown | 422/124 |
| 4,035,451 | 7/1977 | Tringali | 261/101 |
| 4,059,422 | 11/1977 | Steiner | 55/418 |
| 4,166,087 | 8/1979 | Cline et al. | 422/124 |
| 4,294,778 | 10/1981 | DeLuca | 422/124 |

Primary Examiner—Tim R. Miles
Attorney, Agent, or Firm—Christel, Bean & Linihan

[57] ABSTRACT

A device for vaporizing a fluid desired to be introduced into the air by forcibly moving air over the surfaces of an absorptive material which has been impregnated with the fluid desired to be distributed. The device comprises a housing adapted to be attached to a wall or other surface and utilizes a liquid material contained within a hollow container which is so positioned within the housing that the liquid flows into a cup-like member within which a layer of the absorptive material is disposed. The cup-like member includes at least one opening over which air is caused to pass and thereby evaporate the liquid from the absorptive material. A battery powered fan is so positioned as to cause the air to flow past the opening in the cup member and thereby evaporate some of the vaporizable fluid. The entire assembly is contained within a housing which has an air inlet and an air plus vapor outlet, and includes means for properly positioning the several elements in the proper relationship. Also included are indicating means for visually determining the quantity of the vaporizable fluid remaining in the container, and indicating means for showing battery failure, both indicating means being arranged to provide an externally visible indication thereby precluding the need to open the housing to determine fluid quantity or battery failure.

17 Claims, 13 Drawing Figures

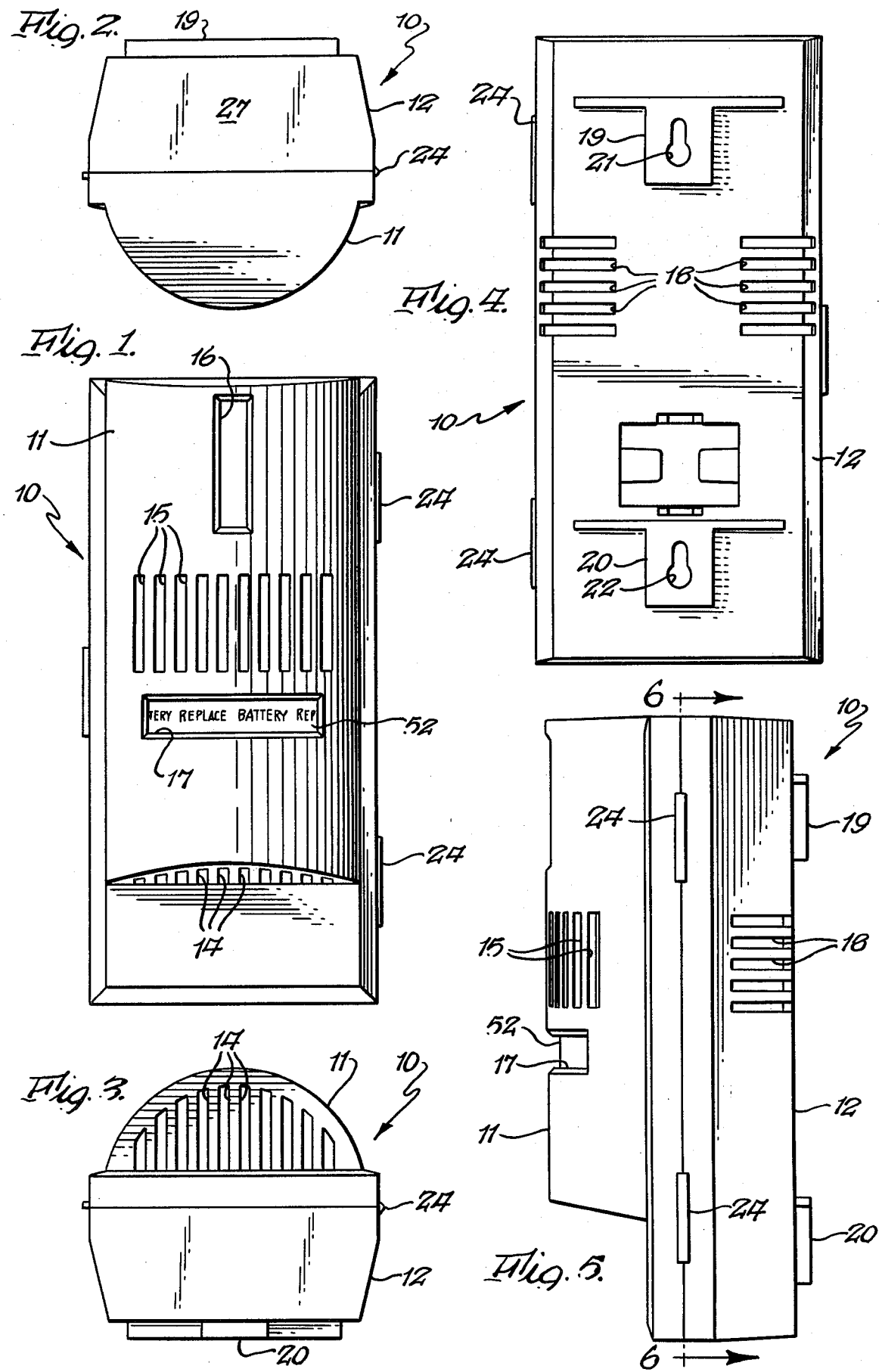

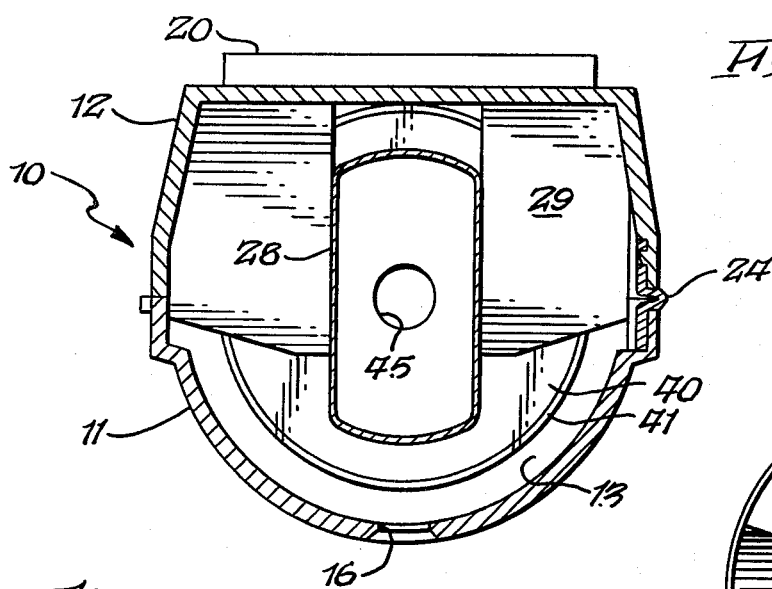
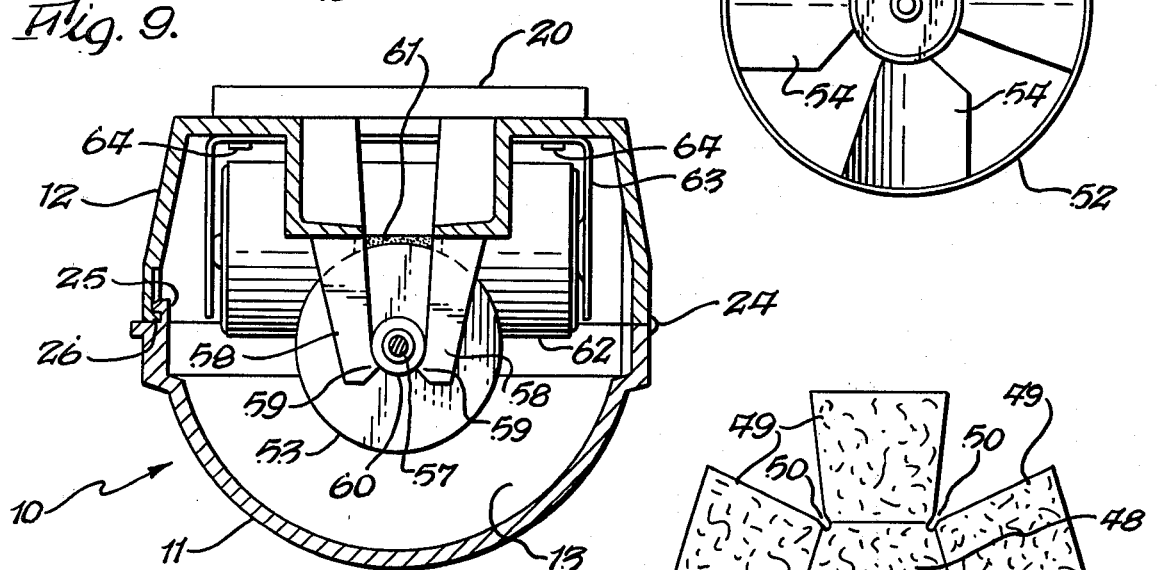
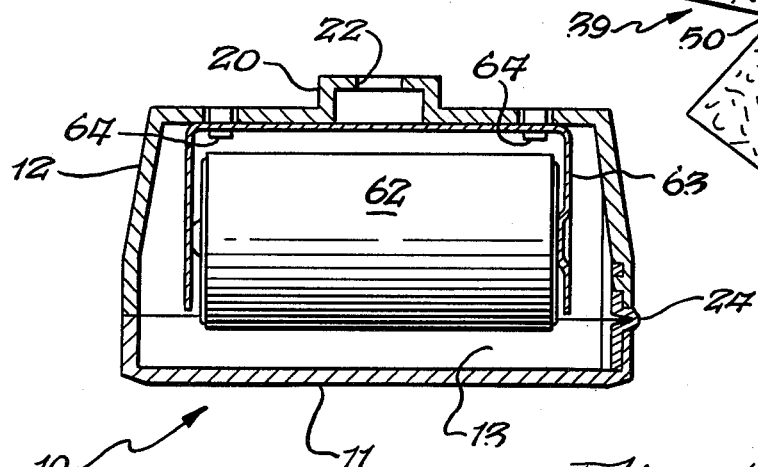
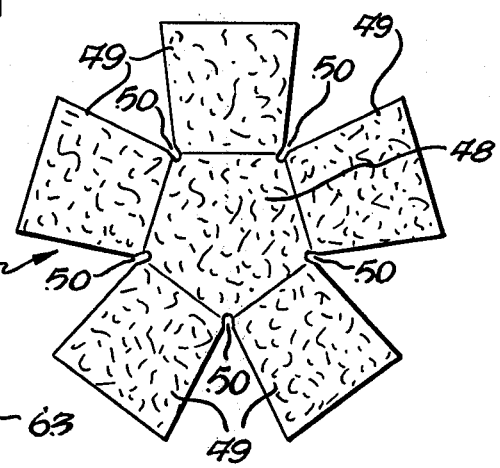

FORCED FLOW VAPOR DISTRIBUTION DEVICE

BACKGROUND OF THE INVENTION

This invention relates to evaporative devices, and more particularly to a device in which a vaporizable liquid is vaporized and mixed with air and then introduced into the desired environment.

The use of vaporizable substances to freshen the air in a room or other enclosed space is well known. A number of devices attempt to accomplish that end, some of which use vaporizable solid materials positioned within a free-standing container that includes apertures to permit the vapor to escape therethrough. The normal convective air currents are utilized to distribute the vapor through the room as the material sublimes and passes through the apertures provided in the container. Although such products are effective to a certain degree, greater effectiveness is obtained when the desired vapors are introduced into the air and distributed in a more forceful fashion than normal convective currents provide. For example, in U.S. Pat. No. 3,990,848, issued Nov. 9, 1976, there is disclosed the use of a battery powered fan which causes the flow of the air through a container within which is positioned a gel-type product which it is desired to introduce into the air. The gel-type product is contained within a porous container which is positioned within the outer container and which also carries a battery. When the material to be vaporized is exhausted the porous container and its associated battery are discarded and a new unit is installed. However, the battery life may exceed the life of the material to be evaporated, or the material may not have been consumed at the time the battery has failed, and in those cases discarding the battery-porous container combination is wasteful and uneconomical.

Another arrangement whereby a vaporizable material may be introduced into the air is disclosed in U.S. Pat. No. 4,035,451, issued July 12, 1977, which discloses a further variation in the concept and involves impregnating an accordian pleated absorptive material with the product to be evaporated and positioning it in a cartridge around a centrally positioned battery, which powers the driving fan. Again, however, failure or exhaustion of one of the two elements of the cartridge requires disposal of the complete cartridge and substitution with a fresh cartridge even though one of the two elements might still be usable.

Additionally, in each of the patented devices described above, there is no direct indication given the user that one of the elements of the cartridge requires replacement. The only way a user can determine if the battery has failed is to attempt to determine whether flow is taking place through the device, which would involve opening the device to ascertain whether the fan was operating. Likewise, the only way a user could determine if the vaporizable material had been exhausted is to somehow determine by odor or otherwise that replacement of the vaporizable material is required.

It is an object of this invention to overcome the deficiencies in the above-described devices and to provide an improved, forced-flow, fan-type evaporative device to introduce a vaporizable material into the air within a predetermined environment, and to facilitate the determination of when either the battery providing the power to drive the fan must be replaced or when the source of the vaporizable material must be replaced in order to continue to obtain the benefits of the device.

SUMMARY OF THE INVENTION

Briefly stated, in accordance with one aspect of the present invention, a forced flow, evaporative device for imparting a vapor to air caused to flow therethrough is provided which includes an enclosed housing having air inlet and outlet ports spaced from each other, a hollow fluid container positioned within the housing and in overlying relationship with a cup member so that the fluid from the container flows into the cup member, a cover plate positioned over the top of the cup member and adapted to receive the neck of the container, the cup member having disposed within it a fluid absorbent material which absorbs the fluid from the product container. The cup member includes a plurality of openings in the side wall adjacent which the absorptive material lies so that air which is forced by an electrically driven fan can pass over the outer surface of the cup member and thereby cause the evaporation of the fluid material sought to be introduced into the air. After vaporization the air-vapor mixture is exhausted through the outlet port and into the area surrounding the device.

BRIEF DESCRIPTION OF THE DRAWINGS

FIG. 1 is a front elevational view of one embodiment of the invention illustrating one form of housing which could be utilized to obtain the benefits of the invention.

FIG. 2 is a top view of the housing shown in FIG. 1.

FIG. 3 is a bottom view of the housing shown in FIG. 1.

FIG. 4 is a rear view of the housing shown in FIG. 1.

FIG. 5 is a side view of the housing shown in FIG. 1.

FIG. 8 is a view taken along the line 8—8 of FIG. 7.

FIG. 9 is a view taken along the line 9—9 of FIG. 7.

FIG. 10 is a view taken along the line 10—10 of FIG. 7.

FIG. 11 is an axial view of the fan utilized in the housing shown in FIG. 1.

FIG. 12 is a plan view of one form of sheet-type absorptive material which is utilized in connection with a cup member having a pentagonal cross section.

DESCRIPTION OF THE PREFERRED EMBODIMENTS

Figure 6:
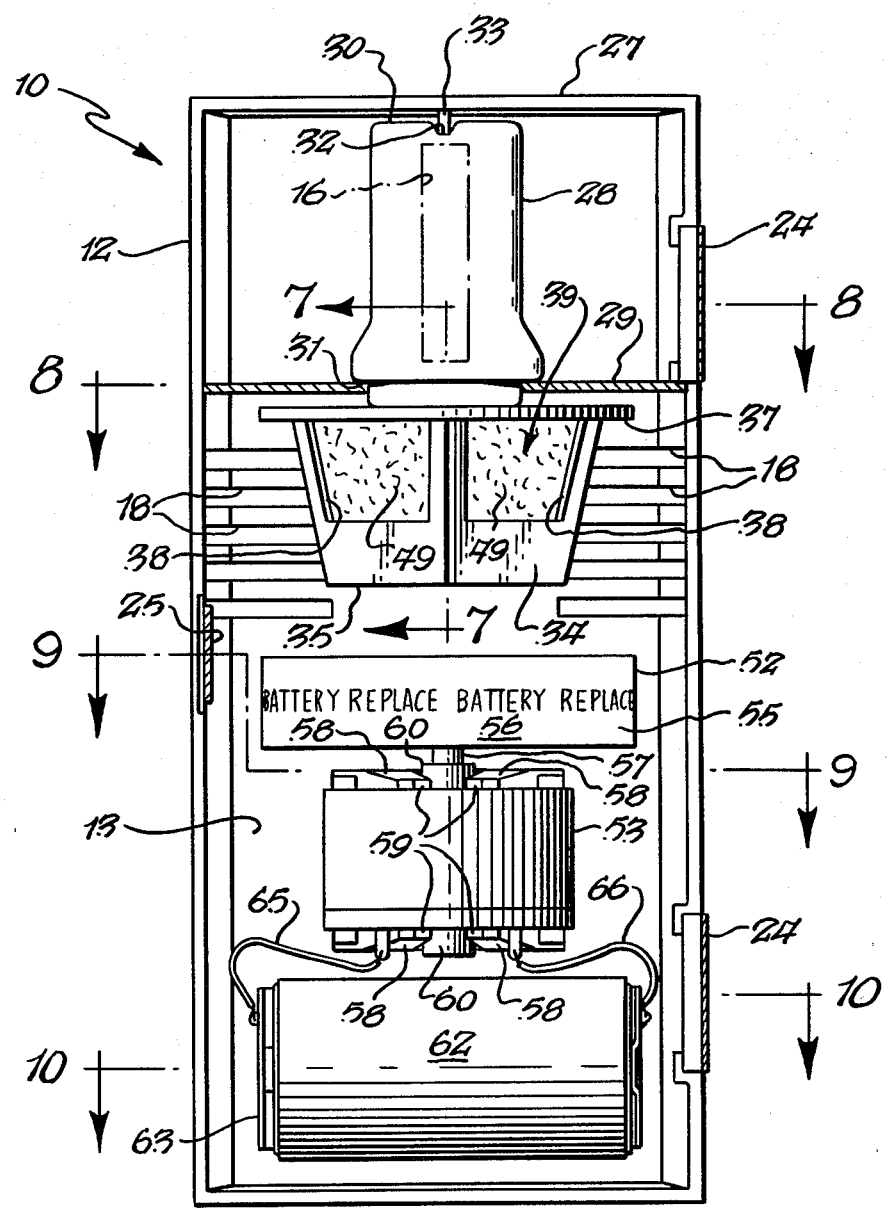
FIG. 6 is a front elevational view of the interior of the housing shown in FIG. 1, partially in cross section, showing the several parts thereof in their operative relationship.

Referring now to the drawings, and particularly to FIGS. 1, 2, and 3 thereof, there is shown an embodiment of the present invention which includes a housing 10 which has a front portion 11 and a rear portion 12, which together define an inner cavity 13 (see FIG. 6) within which the several elements of the device are housed. Front portion 11 includes an air inlet port 14 through which ambient air is caused to flow, and an air outlet port 15 through which the combination of ambient air and vapor is caused to flow. Inlet port 14 and outlet port 15 are shown as a series of parallel rectangular openings, although any particular configuration of openings could be utilized, as desired, the only essential requirement being that there be provided in the housing an inlet opening and an outlet opening, each of which is spaced from the other and each of which is so positioned to permit the inflow and outflow of the air to which the desired substance is to be added. Although in the embodiment shown and described herein the inlet opening is positioned below the outlet opening, it will be apparent to those skilled in the art that those positions could be reversed, if desired, or, alternatively, the openings could be provided in other areas of the housing.

Front portion 11 of housing 10 includes a first viewing means in the form of an elongated rectangular opening 16 which, if desired, can include a transparent or translucent window panel (not shown). Opening 16 permits the display of the quantity of varporizable material contained within housing 10, as will be more fully described hereinafter. A second viewing means in the form of an elongated rectangular opening 17 is provided in an area spaced from opening 16 and positioned between inlet port 14 and outlet port 15. Again, opening 17 can, if desired, include a transparent or translucent window panel (not shown). Opening 17 permits the visual determination of when the battery used to power the fan enclosed within housing 10 must be replaced, as will also be further described hereinafter.

Referring now to FIGS. 4 and 5, rear portion 12 of housing 10 also desirably includes outlet ports 18, so as to facilitate essentially uniform flow of the air-vapor mixture throughout the space within which housing 10 is positioned. Rear portion 12 of housing 10 also includes means to mount the device to a desired surface, such as, for example, a wall, and can include an upper, outwardly, projecting boss 19 and a lower, outwardly projecting boss 20, each of which can include a suitable mounting hole 21, 22, respectively, to permit housing 10 to be securely positioned on a wall over a pair of screws or nails (not shown) which are aligned and are spaced substantially the same distance as are mounting holes 21, 22 in rear portion 12 of housing 10. Also visible from the rear of housing 10 is a mount attaching means 23 for the motor to drive the fan, which will be described in more detail hereinafter.

Front portion 11 and rear portion 12 of housing 10 are preferably molded from a suitable plastic material, which can, for example, be polypropylene, or the like, for ease of manufacture, for reduced cost, and for consumer appeal. Additionally, when made from a plastic material the housing can be given the desired color without the need for a subsequent color application operation, and molded plastic provides a housing which is light in weight, and which permits the configuration of the exterior of the housing to take any of a number of ornamental designs to make the housing visually attractive, as well as functional.

Front portion 11 and rear portion 12 of housing 10 are hingedly connected by a means of a pair of hinges 24 and front portion 11 includes a hooked projection 25 (see FIG. 9) which is adapted to cooperate with a correspondingly but oppositely hooked portion 26 on rear portion 12 of housing 10 to hold the two portions together. When access to the interior of housing 10 is necessary, front portion 11 of housing 10 is released from rear portion 12 and is permitted to pivot about hinges 24 to thereby expose the interior of the device.

Referring now to FIG. 6, there is shown the interior of housing 10 with the several elements of the device in their operative relationship. Positioned adjacent the top wall 27 of housing 10 is a fluid container 28 held in position vertically by a supporting ledge 29, which projects inwardly from rear portion 12 of housing 10. Container 28 includes a base 30 and a shoulder 31. As shown, container 28 is in inverted position with base 30 uppermost and ledge 29 is so sized as to be capable of receiving container 28 and supporting it by means of shoulder 31. The arrangement of ledge 29 and container 28 are shown more clearly in FIG. 8, from which it is apparent that container 28 is of a generally oblong cross section. Although so shown, it is not necessary that that shape be used, and any convenient shape may be utilized, as desired.

As best shown in FIG. 6, container 28 includes a longitudinal groove 32 in base 20, which is adapted to cooperate with a molded-in inwardly projecting ridge 33, which depends from top wall 27 of rear portion 12. The combination of ledge 29, shoulder 31, ridge 33, and groove 32 cooperate to securely position container 28 at the desired location within housing 10. Shown in phantom in FIG. 6 is the outline of opening 16 which is formed in front portion 11 of housing 10 to facilitate the visual determination of the fluid level without the need to open front portion 11. When container 28 is formed from a transparent or translucent material, the level of the liquid within container 28 will be visible through opening 16 and thereby will permit the user to determine when an additional quantity of the evaporative fluid is required. The material from which the container is made can be polypropylene, or any other suitable plastic material which has sufficient resistance to the passage of essential oils, which are an important constituent of the vaporizable materials used in this device.

Figure 7:
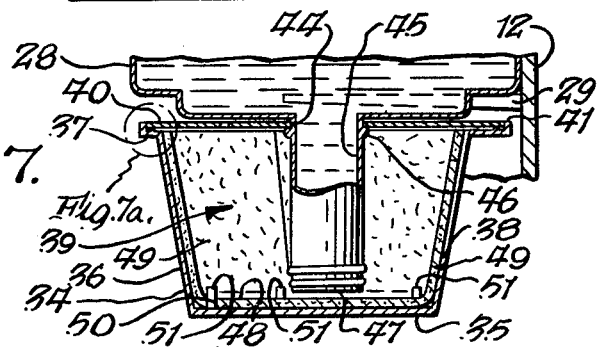
FIG. 7 is a fragmentary cross section of a portion of the interior of the housing shown in FIG. 1 showing the fluid container and the cup member in their desired arrangement, and illustrating the flow path of the vaporizable substance to the absorptive material.
Figure 7A:
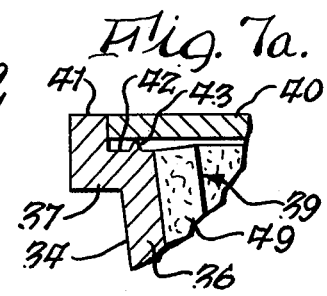
FIG. 7a is a fragmentary cross-sectional view of a portion of FIG. 7, considerably enlarged to show the arrangement of the cover plate and the cup member.

Positioned immediately below container 28 is a cup member 34, the configuration and structure of which is shown in FIGS. 6, 7, and 7a. Cup member 34 consists of a base 35 and an upstanding sidewall 36 which terminates in an outwardly extending lip 37. Sidewall 36 can define either a cup member of circular cross section or it can be of some polygonal cross section, such as, for example, a pentagon, which is the shape shown in the drawings. In any event, sidewall 36 has at least one, and preferably more than one, opening 38 formed therein to permit a fluid absorbent material 34 to be positioned against sidewall 36 and have a substantial portion of its area exposed to the atmosphere outside cup member 34. A cover plate 40 is positioned over cup member 34 and is retained by lip 37 by means of an interference fit with an upwardly extending flange 41 which extends from lip 37. Formed along an upwardly facing surface 42 of lip 37 is a substantially V-shaped sealing ridge 43, which permits a seal to be formed between cover plate 40 and cup member 34.

Cover plate 40 includes a central opening 44 which conforms both in shape and in size with the neck 45 of container 28 and is adapted to cooperatively engage with an outwardly extending bead 46 formed on the exterior of container neck 45 to permit the assembly of cover plate 40 and cup member 34 to be held in position beneath container 28. As shown, container neck 45 is an elongated member and extends within cup member 34 a substantial distance and is preferably positioned so that the outlet 47 of container neck 45 is spaced a short distance above base 35 of cup member 34 to permit fluid from container 28 to fill the base of cup member 34 and thereby permit the fluid to be absorbed by liner 39 of absorptive material disposed within cup member 34. The absorptive liner 39 can be of blotter material or any other fibrous or porous structure which permits the absorption of a relatively large amount of fluid which flows from container neck 45 and fills base 35 of cup member 34. Thus liner 39 will be substantially saturated with fluid that can be caused to be evaporated by the passage of air thereacross.

Since cup member 34 is shown having a pentagonal cross section, liner 39 can be configured as shown in FIG. 12, wherein base portion 48 conforms in shape and size to the cross section of base 35 of cup member 34. Liner 39 includes side portions 49, each of which extends from an edge of base portion 48 and is of generally trapezoidal shape. Side portions 49 are positioned so as to lie against sidewall 36 of cup member 35 and in overlying relationship with openings 38 formed therein. As shown in FIG. 12, liner 39 includes at each apex of base portion 48, indentations 50, which cooperatively engage with upwardly extending positioning lugs 51 provided on the inner surface of base 35 of cup member 34 (see FIG. 7).

Air is caused to flow through housing 10 by means of a fan 52, which is shown in plan view in FIG. 11. Fan 52 is rotated by a motor 53 and causes air to be drawn into housing 10 through air inlet port 14 and thereupon is directed over the outer surface of cup member 34 and through outlet port 15 to be distributed in the ambient environment. As shown, fan 52 has four blades 54, although the number of blades can be varied, as desired. In addition, fan 52 also includes shroud 55 which interconnects the outer edges of each of blades 54 and adds rigidity to the structure. Shroud 55 preferably has sufficient length along the direction of the axis of rotation of fan 52 to permit a printed message to be carried on its outer periphery 56. As shown, in FIGS. 1 and 6, the message can read "REPLACE BATTERY," and that message would only become readable when fan 52 stops rotating. Motor 53 drives fan 52 by means of a drive shaft 57 and is supported by four arms 58 which project inwardly from the inner surface of rear portion 12 of housing 10. The connection arrangement for motor 53 is illustrated in FIG. 9, which shows projecting arms 58, which terminate in inwardly directed gripping members 59, cooperating with hubs 60 which rotatably carry drive shaft 57 of fan 52. Behind motor 53 is a pad 61 of resilient material such as, for example, sponge rubber, urethene foam, or the like, which urges motor 53 outwardly and into firm engagement with gripping members 59. Pad 61 also permits the use of motors of somewhat different size and thereby makes the device more adaptable to the variety of motor sizes available.

Positioned under motor 53 is a battery 62, which is carried by a battery clamp 63 which, in turn, fits over inwardly projecting lugs 64 formed in the inner surface of rear portion 12 of housing 10. The battery can be, for example, a standard "D" size battery, and is preferably of the alkaline variety for longer life. Battery 62 is connected to motor 53 by means of wires 65, 66, which are in contact with respective ends of battery 62 to provide a complete circuit. The battery holding arrangement is shown more clearly in FIG. 10, which shows battery clamp 63 and inwardly projecting lugs 64 which engage corresponding apertures (not shown) in battery clamp 63 and thereby hold it in position.

The hinge arrangement for connecting front portion 4 and rear portion 12 of housing 10 is shown in FIG. 8, which is a cross-sectional view showing hinge 24 as a separate element which is snapped into position in cooperating portions of front panel 11 and rear panel 12. As shown, two hinges 24 are similarly utilized to permit front portion 11 to be swung outwardly, thereby exposing the inner cavity and permitting the replacement of battery 62 or of fluid container 28, as may be required.

In operation, when battery 62 is inserted into battery clamp 63, motor 53 is actuated and fan 52 begins to revolve, thereby drawing air through air inlet port 14 and upward toward and around the outer portion of sidewall 36 of cup member 34, whereupon the air will cause the evaporation of fluid carried by liner 39 and the air-vapor mixture is then forced outwardly through outlet port 15. While fan 52 is rotating, the message carried on outer periphery 56 of shroud 55 is not legible because the speed of the fan is sufficient to cause the message to be a blur. However, when fan 52 stops, as would occur when battery 62 has failed, the message is visible and is displayed through opening 17 in front portion 11, as is shown in FIG. 1. The user of the device then is made aware of the fact that battery 62 requires replacement and a replacement can be readily inserted so that the device can once again be put into operation. Likewise, when the fluid level in container 28 reaches a low level, that fact will be visible through opening 16 and will alert the user that additional fluid is required for the device to function in its intended manner.

As can be seen from the foregoing description and the attached drawings, the present invention provides an improved device for imparting vaporizable substances into an environment. When one or the other of the replaceable elements of the device, either the fluid container or the battery, is exhausted, the particular element which is exhausted can then be replaced without the need for replacing both elements, as was necessary when utilizing the prior art devices. If desired, the vaporizable material can be impregnated in the fluid absorbent material and provided in that form. Alternatively, the vaporizable material can be provided in solid form and positioned in approximately the same area as the cup member herinabove described.

While particular embodiments of the invention have been illustrated and described, it will be apparent to those skilled in the art that various changes and modifications can be made without departing from the spirit and scope of the invention, and it is intended to cover in the appended claims all such changes and modifications that are within the scope of this invention.

What is claimed is:

1. A forced flow evaporative device for imparting a vapor to air forcibly caused to flow therethrough, said device comprising:
   (a) an enclosed housing having air inlet and outlet ports, said inlet ports being spaced from said outlet ports;
   (b) a hollow fluid container positioned within said housing, said container having a shoulder portion terminating in a narrow elongated neck;
   (c) a cup member having a base, an upstanding sidewall extending upwardly from said base and terminating in an open top, and a plurality of apertures in said sidewall, said apertures being spaced from said base and from each other, said cup member being positioned in substantially underlying relationship with said container;
   (d) a cover plate positioned adjacent the top of said upstanding sidewall of said cup member, said cover plate having an aperture to receive said narrow elongated neck of said container;
(e) means for holding said cover plate in fixed relationship to said container;
(f) means for holding said cup member in fixed relationship to said cover plate;
(g) a fluid absorbent material positioned within said cup member and adjacent to said apertures; and
(h) flow inducing means for forcing air to enter said housing through said air inlet, around the periphery of said cup member, and through said outlet.

2. The device of claim 1 wherein said flow inducing means comprises rotary blower means driven by an electric motor.

3. A device of claim 2 wherein said rotary blower means comprises a fan having at least two radially outwardly directed blades.

4. The device of claim 3 wherein said fan blades include a peripheral shroud interconnecting the outermost portions of said blades.

5. The device of claim 4 wherein said housing includes viewing means positioned opposite said shroud and said shroud carries markings on the outer pheriphery thereof, whereby said markings are discernable when said fan is stationary and from a position outside said housing.

6. The device of claim 5 wherein said viewing means comprises a transparent window.

7. The device of claim 6 wherein said electric motor is operated continuously by a battery positioned within said housing.

8. The device of claim 1 wherein said housing includes viewing means positioned opposite said fluid container, whereby the fluid level in said container is observable through said viewing means from a position outside said housing.

9. The device of claim 8 wherein said fluid container carries locating means cooperable with complementary locating means positioned within said housing, whereby to position said fluid container in fixed relationship to said housing.

10. The device of claim 9 wherein said locating means comprises a slot in said container opposite said neck and an inwardly projecting ridge on the inner surface of said housing, said ridge being aligned with said slot and in interengaging relationship therewith, and wherein said housing includes at least one inwardly projecting container support member adapted to cooperate with said shoulder portion of said container, whereby to firmly position said container with respect to said housing.

11. The device of claim 10 wherein said cup member is of polygonal cross section comprising at least three substantially flat, interconnected wall members defining said upstanding sidewall, each of said wall members having at least one opening therein, said absorbent material comprising a thin sheet including a center portion substantially conforming with the cross section of the base of said cup member, and a plurality of arms, each of which extends from a respective edge of said center portion, said center portion positioned adjacent to the base of said cup member and said arms positioned adjacent to said wall members and in overlying relationship to the respective apertures therein.

12. The device of claim 11 wherein said cup member includes at least one locating pin positioned on the inner surface thereof and said absorbent material includes at least one aperture cooperable with said locating pin to position said absorbent material in relationship to said cup member.

13. A forced flow evaporative device for imparting a vapor to air forcibly caused to flow therethrough, said device comprising:
(a) an enclosed housing having air inlet and outlet ports, said inlet ports being spaced from said outlet ports, said housing including viewing means;
(b) means for supporting a vaporizable material between said inlet ports and said outlet ports;
(c) flow inducing means for forcing air to enter said housing through said air inlet, around the periphery of said vaporizable material supporting means, through said outlet, said flow inducing means including indicia visible through said viewing means to provide an externally visible indication of operation cessation of said flow inducing means.

14. The device of claim 13 wherein said viewing means is positioned between said inlet ports and said outlet ports.

15. The device of claim 13 wherein said flow inducing means comprises rotary blower means driven by an electric motor.

16. The device of claim 15 wherein said rotary blower means comprises a fan having at least two radially outwardly directed blades.

17. The device of claim 16 wherein
(a) said fan includes a peripheral shroud interconnecting the outermost portions of said fan blades;
(b) said viewing means comprises a transparent window supported in the housing opposite said shroud; and
(c) said indicia are positioned on the outer periphery of said shroud and include a message which is illegible through said window when said flow inducing means are operating and is legible when said flow inducing means have ceased operating.

* * * * *